US008008477B2

(12) United States Patent
Fuertes

(10) Patent No.: US 8,008,477 B2
(45) Date of Patent: *Aug. 30, 2011

(54) METHOD FOR PREPARING A COMPOSITION CONTAINING AT LEAST ONE INTERNAL DEHYDRATION PRODUCT FOR A HYDROGENATED SUGAR

(75) Inventor: Patrick Fuertes, Lambersart (FR)

(73) Assignee: Roquette Freres, Lestrem (FR)

( * ) Notice: Subject to any disclaimer, the term of this patent is extended or adjusted under 35 U.S.C. 154(b) by 154 days.

This patent is subject to a terminal disclaimer.

(21) Appl. No.: 12/118,885

(22) Filed: May 12, 2008

(65) Prior Publication Data

US 2008/0213439 A1 Sep. 4, 2008

Related U.S. Application Data

(62) Division of application No. 10/299,138, filed on Nov. 19, 2002, now abandoned.

(30) Foreign Application Priority Data

Nov. 20, 2001 (FR) ...................................... 01 15018

(51) Int. Cl.
*C07H 1/00* (2006.01)
(52) U.S. Cl. ........................................................ 536/124
(58) Field of Classification Search .................. None
See application file for complete search history.

(56) References Cited

U.S. PATENT DOCUMENTS

| 2,891,004 | A | 6/1959 | Judson |
| 3,160,641 | A | 12/1964 | Hartmann |
| 3,223,752 | A | 12/1965 | Tate et al. |
| 4,082,881 | A | 4/1978 | Chen et al. |
| 4,371,703 | A | 2/1983 | Stoss |
| 4,383,051 | A | 5/1983 | Meyborg et al. |
| 4,408,061 | A | 10/1983 | Salzburg et al. |
| 4,418,174 | A | 11/1983 | Dhein et al. |
| 4,529,666 | A | 7/1985 | Salzburg et al. |
| 4,564,692 | A | 1/1986 | Feldmann et al. |
| 4,861,513 | A | 8/1989 | Lueders et al. |
| 5,766,679 | A | 6/1998 | Siemensmeyer et al. |
| 5,969,015 | A | 10/1999 | Zinke et al. |
| 6,013,812 | A | 1/2000 | Haas et al. |
| 6,025,061 | A | 2/2000 | Khanarian et al. |

FOREIGN PATENT DOCUMENTS

| CA | 1 178 288 | 11/1984 |
| EP | 0 315 334 | 12/1992 |
| GB | 613 444 | 11/1948 |
| WO | 99/45060 | 9/1999 |
| WO | 00/14081 | 3/2000 |

OTHER PUBLICATIONS

Derwent abstract of EP1106616, 2001
Derwent abstract of WO99/45054, 1999.
Derwent abstract of EP0323994, 1989.
Derwent abstract of EP0380402, 1990.
Derwent abstract of WO 99/33776, 1999.
Kricheldorf, J. of Macromol. Sc., C 37(4), pp. 599-631 (1997).
Ullmann's Encyclopedia, $5^{th}$ Ed., pp. 687-716, A22 (2001).
Plastics Additive Handbook, $5^{th}$ Ed., Chap 1, "Antioxidants," pp. 1-139 (2001).
Plastics Additive Handbook, $5^{th}$ Ed., Chap. "Acid scavengers," pp. 485-509 (2001).
Kirk-Othmer, Encycl. of Chemical Tech., $4^{th}$ Ed., vol. 5, pp. 764-795 (1993).
A partial English translation of the "European Parliament and Council Directive No. 95/2/EC of Feb. 20, 1995".
Patent Abstracts of Japan, vol. 1998. No. 03, JP09286787 (New Japan Chemical Co.) (1998).

*Primary Examiner* — Elli Peselev
(74) *Attorney, Agent, or Firm* — Young & Thompson

(57) ABSTRACT

The subject of the present invention is a novel method for preparing a composition of internal dehydration product of a hydrogenated sugar, comprising:
a) a step of distilling a medium containing the said internal dehydration product in order to obtain a distillate enriched with this product,
b) optionally, at least one subsequent step of purifying the distillate thus obtained,
c) a subsequent step of bringing the distillate obtained during step a), and then optionally subjected to step b), into contact with an agent capable of improving the stability of the internal dehydration product predominantly contained in the distillate, the said agent not being in gaseous form,
d) optionally, a subsequent step of shaping the resulting composition of internal dehydration product of a hydrogenated sugar.

This method makes it possible in particular to obtain a stable isosorbide composition, characterized by its purity and/or its content of certain stabilizing or nonstabilizing species.

12 Claims, No Drawings

METHOD FOR PREPARING A COMPOSITION CONTAINING AT LEAST ONE INTERNAL DEHYDRATION PRODUCT FOR A HYDROGENATED SUGAR

This is a Divisional Application of U.S. application Ser. No. 10/299,138, filed Nov. 19, 2002, now abandoned, which claimed priority to French Application FR 01/15018 filed Nov. 20, 2001.

The present invention concerns a novel method for preparing a composition containing at least one internal dehydration product of a hydrogenated sugar.

It also relates to the use of the composition thus prepared in the preparation of polymeric or nonpolymeric, biodegradable or nonbiodegradable products or mixtures intended in particular for the chemical, pharmaceutical, cosmetic or food industries.

Finally, the present invention also concerns, as a novel product which can be obtained according to the said method, a composition of the type in question having specific characteristics, especially in terms of stability, purity and/or content of certain stabilizing or nonstabilizing species.

The expression "hydrogenated sugar" for the purposes of the present invention is understood to mean in particular:
- hexitols such as, for example, sorbitol, mannitol, iditol and galactitol,
- pentitols such as, for example, arabitol, ribitol and xylitol, and
- tetritols such as, for example, erythritol.

The expression "internal dehydration product" is understood to mean any product resulting, in any manner, in one or more steps, from the removal of one or more molecules of water from the original internal structure of a hydrogenated sugar such as those mentioned above.

This may advantageously be internal dehydration products of hexitols, in particular of dianhydrohexitols or "isohexides" such as isosorbide (1,4-3,6-dianhydrosorbitol), isomannide (1,4-3,6-dianhydromannitol) or isoidide (1,4-3,6-dianhydroiditol).

Among these doubly dehydrated hydrogenated sugars, isosorbide is currently the one for which the largest number of industrial applications is being developed, or at the very least envisaged. They relate to in particular:
- the preparation of isosorbide 2-nitrate, 5-nitrate or 2,5-dinitrate, which are useful in the therapeutic treatment of diseases, in particular cardiac and/or vascular diseases—as described in U.S. Pat. No. 4,371,703;
- the preparation of alkylated, in particular dimethylated, derivatives of isosorbide, which are useful in particular as solvents in the context of the preparation of pharmaceutical or cosmetic compositions (U.S. Pat. No. 4,082,881), or even as active ingredients in compositions for oral hygiene (EP patent 315 334);
- the preparation of isosorbide derivatives which can be used in detergent compositions for fuels (EP patent 1 106 616),
- the preparation of alkylated or alkenylated derivatives which can be used as plasticizers for polymers, adhesives or inks (patent WO 99/450060),
- the preparation of specific biphosphites which can be used as stabilizing agents for polymers or lubricants (FR patent 2 757 517)
- the preparation of articles based on polyvinyl alcohol (U.S. Pat. No. 4,529,666), polyurethanes (U.S. Pat. No. 4,383,051), or polyesters also containing monomer units of the "terephthaloyl" type (patents U.S. Pat. No. 3,233,752 and U.S. Pat. No. 6,025,061);
- the preparation of polycondensates as described in the article by H. R. KRICHELDORF published in the Journal of Macromolecular Science—REV. MACROMOL. CHEM. PHYS., C 37 (4), 599-631 (1997),
- the preparation of biodegradable polycondensates (patent WO 99/45 054);
- the preparation of aqueous lacquers (U.S. Pat. No. 4,418,174) or of compositions with surface covering and/or colouring action (U.S. Pat. No. 5,766,679).

For the majority of the abovementioned applications of isosorbide and other internal dehydration products of hydrogenated sugars, in particular the other isohexides, it is generally required to apply a purification treatment to the compositions resulting directly from the actual dehydration step. This is in particular because any hydrogenated sugar subjected to such a step (for example sorbitol) is likely, during the said step, to be converted to, apart from the desired dehydration product (for example isosorbide), various coproducts such as:
- isomers of the said desired product, for example isomers of isosorbide such as isomannide and isoidide,
- products which are less dehydrated than the desired product or than its isomers, for example sorbitan, mannitan or iditan,
- derivatives resulting from the oxidation or more generally from the degradation of the abovementioned products, it being possible for these derivatives to include, for example when the desired product is isosorbide, coproducts of the type such as deoxymonoanhydrohexitols, monoanhydropentitols, monoanhydrotetritols, anhydrohexoses, hydroxymethylfurfural, or glycerin,
- derivatives resulting from the polymerization of the abovementioned products, and/or
- highly coloured species of a poorly defined nature.

It should be recalled that, in general, all or some of these various categories of coproducts or impurities are generated to a greater or lesser degree during the actual step of dehydration of the hydrogenated sugar, this being independently of the conditions and precautions used in practice during the said step, and for example independently:
- of the nature and of the form of presentation of the dehydration acid catalyst used (inorganic acid, organic acid, cationic resin, and the like), or
- of the quantity of water or of organic solvent(s) in the initial reaction medium, or
- of the purity of the hydrogenated sugar, for example sorbitol, composition used as raw material.

Various technologies have been recommended for the purposes of obtaining compositions derived from the said dehydration step, for example compositions of isohexide(s), which are improved in terms of purity, this being in a "direct" manner by adjusting the reaction conditions during the said step and/or in an "indirect" manner by applying one or more purification treatments after the said step.

CA patent 1 178 288 recalls on its page 14, lines 3-8 that it is recommended to carry out the actual dehydration reaction under an inert gaseous atmosphere in order to avoid oxidation reactions, in particular when relatively high temperatures and long reaction times are envisaged.

U.S. Pat. No. 4,861,513 describes a sorbitol dehydration reaction carried out simultaneously in the presence of an inert gas (nitrogen) and a reducing agent (sodium hypophosphite) for the preparation of particular mixtures of polyols, which have a low content (10 to 26%) of dianhydrosorbitol.

For its part, GB patent 613,444 describes the production, by dehydration in a water/xylene medium, of an isosorbide composition which is then subjected to a treatment of distillation and then of recrystallization from an alcohol/ether mixture.

A purification treatment combining distillation and recrystallization from a lower aliphatic alcohol (ethanol, methanol) has also been recently recommended in patent WO 00/14081. This document moreover indicates that, in the case where distillation is the only purification step envisaged, it is advantageous to carry out the said step in the presence of sodium borohydride.

The passage on page 11, lines 13-21 of the said patent describes the distillation "in an inert atmosphere (argon)" of an isosorbide composition previously brought into contact with sodium borohydride (NaBH4).

According to table 1 of this patent, it appears that this distillation makes it possible to increase the purity of the initial product ("C-ISOS") by a value of 98.79 to 99.07%.

Other authors have also recommended that the distillation step be carried out in the presence of a boron-containing compound, in particular of boric acid or of an anionic resin previously charged with borate ions, as described in U.S. Pat. No. 3,160,641.

Patents U.S. Pat. No. 4,408,061 and EP 323,994 envisage the use of particular dehydration catalysts (gaseous hydrogen halide and liquid hydrogen fluoride respectively), advantageously combined with carboxylic acids as cocatalysts followed by the distillation of the crude isosorbide or isomannide compositions thus obtained.

U.S. Pat. No. 4,564,692 mentions, without giving any details, prepurification on "ion exchangers and/or activated charcoal" of isosorbide or isomannide compositions followed, after concentration by evaporation and seeding of crystals of the desired isohexide, by crystallization thereof from water.

EP patent 380,402 claims, for its part, the dehydration of hydrogenated sugars in the presence of hydrogen under pressure and of particular catalysts based on a combination between copper and a noble metal of Group VIII or gold. These conditions are presented as making it possible to significantly reduce the formation of impurities of a polymeric nature during the actual dehydration step.

More recently, there has been described in EP patent 915,091 the possibility of further advantageously reducing the genesis of such undesirable polymers, this being by using acid-stable hydrogenation catalysts during the dehydration step.

However, the abovementioned documents do not relate specifically to the questions of stability over time of the purified compositions thus obtained and which have to be marketed, in particular to their stability over time under conventional conditions of storage temperature, i.e. generally between 0 and 40° C.

This results from the fact that isosorbide is generally considered, as underlined on page 600, point 4. of the abovementioned article by H. R. KRICHELDORF, as an aliphatic diol which is particularly chemically and thermally stable.

At the end, nevertheless, of an in depth study of these questions, the Applicant Company has first of all made the double observation according to which:
1) not only was the level of stability of a composition as envisaged here, for example an isosorbide composition, not correlated with its level of purity,
2) but further, the use of an agent such as gaseous nitrogen or sodium borohydride as described in the prior art, i.e. at the latest at the time of the distillation step, did not make it possible to significantly improve this stability.

And it is while further pursuing these studies that the Applicant Company found that, surprisingly and unexpectedly, only the use a) of specific stabilizing agents, in this case in nongaseous form, and b) at a particular time of the method of preparation, in this case after the actual distillation step, made it possible to achieve this aim and in particular to prepare isosorbide compositions whose behaviour during storage, at least at ambient or moderate temperature, was improved. For these studies, the Applicant Company developed a test for stability during storage at 40° C. which will be described later and which makes it possible to more rapidly evaluate the stability of compositions which, in the industrial reality, are generally stored at lower temperatures, i.e. at room temperature.

Accordingly, the present invention concerns a method for preparing a composition of internal dehydration product of a hydrogenated sugar, the said method being characterized in that it comprises:
  a) a step of distilling a medium containing the said internal dehydration product in order to obtain a distillate enriched with this product,
  b) optionally, at least one subsequent step of purifying the distillate thus obtained,
  c) a subsequent step of bringing the distillate obtained during step a), and then optionally subjected to step b), into contact with an agent capable of improving the stability of the internal dehydration product predominantly contained in the distillate, the said agent not being in gaseous form,
  d) optionally, a subsequent step of shaping the resulting composition of internal dehydration product of a hydrogenated sugar.

The agent used during step c) subsequent to step a) of distillation properly speaking (hereinafter "improving agent") may be of a varied nature.

In accordance with the present invention, it cannot consist of an agent of a gaseous nature such as nitrogen gas, in any case not solely of such an agent.

The Applicant Company indeed observed, as will be moreover exemplified, that the fact that an isosorbide composition was stored under an inert atmosphere such as nitrogen gas without introducing therein an improving agent in accordance with the invention, did not make it possible, in the end, to obtain an isosorbide composition whose stability over time was truly improved in relation to the same product stored under air.

According to a first variant of the invention, the improving agent used in the abovementioned step c) is chosen from the group comprising reducing agents, antioxidants, oxygen scavengers, light stabilizers, anti-acid agents, metal-deactivating agents and any mixtures of at least any two of these products.

All these agents may be of a natural or synthetic origin, of an inorganic or organic nature.

The expression "reducing agents" is understood to mean any compound having electron donating properties.

These compounds may correspond to those described in the chapter entitled "Reduction" on pages 687 to 716, Volume A22 of the 5th edition of the book "Ullmann's Encyclopedia of Industrial Chemistry" (1993) VCH Verlagsgesellschaft mbH, Weinheim (Germany).

They may be in particular compounds based on boron or aluminium such as the boron or aluminium hydrides described on pages 699-703 of the abovementioned chapter and in particular sodium borohydride (NaBH4) or lithium aluminium hydride (LiAlH4).

The Applicant Company has discovered, as will be moreover exemplified, that in contrast to its use before step a) of distillation, the use of NaBH$_4$ in the abovementioned step c), i.e. after distillation, made it possible to obtain an isosorbide composition whose stability was significantly improved.

The reducing agent used in accordance with the invention may also consist of a compound based on phosphorus such as a phosphine or a phosphite.

The improving agent may also be chosen, as indicated above, from antioxidants. The expression "antioxidants" is understood to mean in particular any compound directly or indirectly capable of limiting or even preventing, regardless of its mode of action, the complex phenomena of oxidation, including autooxidation, of organic substances of natural or synthetic origin, of a monomeric or polymeric nature.

These compounds may correspond to those described in chapter 1 entitled "Antioxidants" of the 5th edition of the book "Plastics Additives Handbook" (2001) Carl Hanser Verlag, Munich (Germany) or to any mixture of at least any two of these compounds.

Such compounds may act according to at least one of the mechanisms described on pages 10 to 19 of the said chapter and may have a chemical structure in accordance with one of those presented in the passage corresponding to pages 97 to 139 of the said chapter.

They may be in particular compounds based on nitrogen, in particular aromatic or nonaromatic amines, further containing, or not, at least one alcohol functional group.

They may be in particular hydroxylamine, morpholine, derivatives thereof and/or one of the compounds described under the codes "AO-7", "AO-15", "AO-16", "AO-26" to "AO-28" and "AO-35" to "AO-41" of the abovementioned passage.

The antioxidant which may be used as improving agent for the purposes of the invention may also consist of a nitrogenous or non-nitrogenous aromatic compound containing or not at least one alcohol functional group, and may consist, for example, of phenolic compounds such as hydroquinone, phenol, tocopherols and the respective derivatives thereof and/or of one of the compounds described in the abovementioned passage under the codes "AO-1" to "AO-42".

They may be in particular, 2,6-di-tert-butyl-4-methylphenol (BHT), hydroquinone or mixtures thereof.

The expression "tocopherols and derivatives" is understood to mean in particular all the products described in patent WO 99/33776 in the name of the Applicant, in particular in the passage on page 11, line 14 to page 12, line 11 of the said patent. They may advantageously be a compound wholly or partly consisting of α-tocopherol and in particular of vitamin E.

Furthermore, the improving agent used in accordance with the invention may consist of an antioxidant compound based on phosphorus or on sulphur such as those described in the abovementioned chapter of "Plastics Additives Handbook", for example under the codes "PS-1" to "LPS-12" and "TS-1" to "TS-4".

It may in particular be chosen from the group comprising phosphites, phosphonites, sulphites, the salts of esters of thiodipropionic acid and mixtures thereof.

The improving agent for the purposes of the present invention may also consist, as indicated above, of a light stabilizer. This definition includes the compounds described on page 141 to 425 of "Plastics Additives Handbook" cited above, in particular the compounds based, or not, on nitrogen or sulphur, which are aromatic or not, containing or not at least one alcohol functional group, which are mentioned therein, in particular under the codes "UVA-1" to "UVA-27" and "HA(L)S-1" to "HA(L)S-52".

The improving agent may also be chosen from anti-acid agents, this definition including the compounds described in the chapter entitled "Acid Scavengers" on pages 485 to 510 of the book "Plastics Additives Handbook" cited above.

This definition also includes alkaline agents, in particular those which are capable of being used as "buffers" in neutral or alkaline media and in particular in media having a pH of the order of about 7 to 9.

The alkaline agents may in particular consist of alkali metal, in particular sodium or potassium, hydroxides, carbonates, borates or phosphates.

They may, by way of examples, be chosen from the group comprising sodium hydroxide, potassium hydroxide, sodium carbonate, potassium carbonate, sodium metaborate, disodium phosphate and any mixtures of these products.

Finally, the said improving agent may advantageously be chosen from metal-deactivating agents, this definition including the compounds termed "Metal Deactivators" as described on pages 18 and 113 of the said book but also the compounds described in the chapter entitled "CHELATING AGENTS" on pages 764 to 795, Volume 5 of the 4th edition of the book "KIRK-OTHMER ENCYCLOPEDIA OF CHEMICAL TECHNOLOGY" (1993) John Wiley & Sons, Inc.

These metal-deactivating agents may consist in particular of metal-complexing or -chelating agents of natural origin, in particular containing at least one alcohol functional group, and in particular obtained from starchy substances such as gluconates, glucoheptonates, phytates, lactates or citrates.

The Applicant Company has in particular found that the said agent could advantageously be capable of complexing or chelating metals such as iron, copper, cobalt, manganese or nickel. In industrial practice, in particular during manufacturing, forming and storage operations, it is difficult to avoid all metal contamination in such compositions.

According to another variant of the invention, in particular when the composition of the internal dehydration product should be subjected to severe regulatory constraints, the improving agent may be advantageously chosen from the products authorized as food additives, in particular those termed "antioxidants", "acidity regulators" or "sequestrants" within the meaning of the European regulations, in particular of Directive 95/2/EC of the European Parliament and of the Council of 20 Feb. 1995 and of subsequent amendments thereof.

The improving agent may then in particular be chosen from the group comprising ascorbic acid (vitamin C), erythorbic acid, lactic acid, citric acid, gallic acid, tocopherols, derivatives (in particular salts) of all these products, BHT, butylated hydroxyanisole (BHA) and any mixtures of these products.

The improving agent may be used in step c) in very small proportions, namely of the order of 0.0001% (1 ppm) to 2%, these percentages being expressed by dry weight of improving agent relative to the dry weight of the internal dehydration product of a hydrogenated sugar then predominantly present in the distillate, for example isosorbide, then present in this medium.

According to a first variant of the method according to the invention, the improving agent is used in step c) of the said method in an amount of 0.001 to 2%, preferably 0.002 to 1.5% and still more preferably 0.003 to 1.5%.

The Applicant Company has found in particular that this amount of introduction could advantageously be between 0.005 and 1%, for example when the improving agent consisted of NaBH$_4$ or an antioxidant such as BHT, morpholine, hydroxylamine, vitamin C, hydroquinone, sodium erythorbate or compounds described under the codes "A0-18" or "PS-2" in the abovementioned literature.

According to another variant of the method according to the invention, the improving agent is used in step c) of the said method in an amount of 0.0001 (1 ppm) to 0.5%, preferably 0.0003 (3 ppm) to 0.3%.

The Applicant Company has in particular found that this rate of introduction could advantageously be between 0.0003 (3 ppm) and 0.1% when the improving agent consisted of a reducing agent such as $NaBH_4$ or of an anti-acid agent such as an alkaline agent like sodium metaborate or disodium phosphate.

Such low levels of improving agent, for example of 0.0003% (3 ppm) to 0.01% (100 ppm) of $NaBH_4$ or of another sodium salt, may in particular be advantageously used for the purpose of satisfying, in addition, technical and/or regulatory constraints which may exist depending on the particular application for which the stabilized composition in accordance with the invention is intended.

In the context of the method according to the invention, it should be specified that the medium subjected to step a) of distillation may be of a highly varied nature, including in terms of dry matter content, of temperature and/or of purity in relation to the desired dehydration product.

It may be, according to a first variant, an isosorbide composition consisting of the medium directly derived from the actual dehydration reaction and having a purity in relation to the desired product, for example in relation to isosorbide, of the order of 50 to 80%.

According to another possibility, the said composition may, because in particular it already results from one or more previous purification operations, in particular by distillation and/or crystallization, have a purity in relation to the desired product, for example in relation to isosorbide, of greater than 80%.

Advantageously, step a) of distillation is followed by a step b) of purification of the resulting distillate.

According to a first variant, step b) consists of a purification step according to which the distillate, generally dissolved in solution, is treated with at least one purification means chosen from decolorization means and ion-exchange means.

The expression "decolorization means" is understood to mean in particular activated charcoal in granular or pulverulent form and adsorption resins.

By way of example, it is possible to use, alone or in combination, granular activated charcoal such as the product "CECA DC 50", pulverulent activated charcoal such as the product "NORIT SX +" and/or a resin such as those called "DUOLITE XAD 761", "MACRONET MN-600" or "MACRONET MN-400".

The expression "ion-exchange means" is understood to mean in particular weak or strong anionic resins, and weak or strong cationic resins.

By way of example, it is possible to use, alone or in combination, a strong anionic resin such as the resin "AMBERLITE IRA 910" or a strong cationic resin such as the resin "PUROLITE C 150 S".

The ion-exchange means may advantageously comprise at least one anionic resin and at least one cationic resin. Preferably, this means is composed of a mixed bed of anionic and cationic resin(s) or a succession of cationic and then anionic resin(s) or a succession of anionic and then cationic resin(s).

Preferably, during step b) of the method in accordance with the invention, the distillate obtained during step a) is treated, in any order, with at least one activated charcoal and with at least one ionic or nonionic resin.

Very advantageously, the said distillate is first treated with activated charcoal and then with at least one resin and then again with activated charcoal.

According to another variant of the method according to the invention, the Applicant Company has found that it was particularly advantageous for the composition subjected to step b) of purification to already have certain characteristics in terms of maximum content of particular impurities, for example of formic acid and of species of the "monoanhydrohexose" type.

It also found that such a content could in particular be ensured by directly subjecting the distillate obtained during step a) to the said step b) of purification.

The method according to the invention may therefore be characterized in that the distillate subjected to the said step b) has a formic acid content of less than 0.002% (20 ppm) and a content of monoanhydrohexoses of less than 0.02% (200 ppm), these percentages being expressed by dry weight relative to the dry weight of the internal dehydration product of a hydrogenated sugar then predominantly present in the said distillate, for example to the dry weight of isosorbide present in the said distillate.

The distillate may in particular have a formic acid content of less than 0.0005% (5 ppm) and a content of monoanhydrohexoses of less than 0.005% (50 ppm).

According to another variant and advantageously, the improving agent used according to the invention is used directly after step b) of purification and in particular, as will be further exemplified, introduced directly into the purified aqueous solution of internal dehydration product derived from step b), which solution generally has a temperature at most equal to 60° C.

Regardless of the mode of operation of the method which is the subject of the invention, the Applicant Company also found that it could be advantageous for all or part of step c), during which the improving agent is present, to be carried out in a medium which is liquid and whose temperature is at least equal to the softening or melting temperature of the desired internal dehydration product (for example isosorbide) but less than about 140° C.

This temperature may, in particular in the case of isosorbide, be between 60 and 135° C.

These conditions improve the homogeneous distribution of the improving agent in the resulting composition, in particular if the latter has to be cooled and then shaped in accordance with the optional step d).

In this regard, the Applicant Company thinks that it may be advantageous for the said improving agent to have minimal solubility in water and/or in the desired internal dehydration product.

In particular, the present invention may also be characterized in that the said improving agent has a solubility, in water at 20° C., at least equal to 0.01%, preferably at least equal to 0.1%.

After step c) and as indicated above, the composition of internal dehydration product of a hydrogenated sugar obtained according to the invention may be shaped during a subsequent step d).

This step may consist of an operation of pelleting or scaling of the crystallized mass or "massed product" resulting from cooling, in particular by contact with a cold surface, of the composition derived from step c).

Step d) of shaping may, if desired, be followed by a step of grinding and/or sieving, this being before any step of storing and/or packaging in bags the composition thus obtained.

According to another variant, the composition of internal dehydration product of a hydrogenated sugar obtained according to the invention may, after step c), be stored as it is, in particular in the liquid or paste state, with no subsequent specific shaping step.

The composition resulting from the method according to the invention may moreover have been subjected, at any moment, to a concentration step, in particular a step of evaporation under vacuum, the said step being performed under the mildest possible conditions, in particular in terms of duration and temperature.

According to a first variant, the said concentration step is carried out, completely or partly, simultaneously with step c) in accordance with the invention.

According to another variant, the said concentration step is carried out, completely or partly, prior to step c) in accordance with the invention, preferably immediately before the said step c).

In any case, it is advantageous to carry out the said concentration step directly after step b) of purification, as soon as this step b) has been carried out.

Accordingly, regardless of the moment when one concentration step at least has been carried out in the context of the method in accordance with the invention, including therefore prior to step c), the said method makes it possible to prepare a stable liquid composition of internal dehydration product of a hydrogenated sugar, in particular a stable liquid isosorbide composition, whose dry matter ("DM") content is high, i.e. between 50 and 90%, in particular between 75 and 88%.

This DM may in particular be of the order of about 85%.

All the steps of the method according to the invention, obligatory or optional, which have just been described may in addition, if desired, be carried out under an inert atmosphere, including step c) characteristic of the present invention and/or any subsequent step, in particular of shaping, of storing or of packaging in bags.

Accordingly, a new means is available which is capable of providing a composition of an internal dehydrogenation product of a hydrogenated sugar, for example an isosorbide composition, whose stability is improved, such a stability being required regardless of the uses for which the said composition is intended and regardless moreover of the purity of the said composition.

It is remarkable to underline that the method according to the invention makes it possible to obtain in particular a composition of the type in question which, although having a purity which is indeed high but nonoptimum, is found to be stable. The expression "stable composition" for the purposes of the present invention is understood to mean a composition which, when stored in a noninert atmosphere for a period of at least one month and at a temperature of 40° C., has both a formic acid content of less than 0.0005% (5 ppm) and an overall content of monoanhydrohexoses of less than 0.005% (50 ppm), these percentages being expressed by dry weight relative to the dry weight of the said composition. This stability may obviously be very significantly greater than 1 month and may be up to at least two months, preferably at least 6 months and still more preferably at least one year; which means that, under normal storage conditions, i.e. at room temperature, the compositions according to the invention can be stored for significantly longer periods than those mentioned above.

A novel product is henceforth available, inter alia, which consists of a composition of isosorbide or another internal dehydration product of a hydrogenated sugar, which is stable according to the definition which has just been given and which simultaneously has a purity of less than 99.8%, which is in particular between about 98.0 and 99.7%.

Remarkably, the said composition has a stability of at least two months, preferably of at least six months, and still more preferably of at least one year.

The Applicant Company has in particular found that a composition in accordance with the invention was most particularly capable of having such a stability so long as it had a pH greater than 5, preferably greater than 6 and in particular of between about 6.5 and 9.5, regardless of its form of presentation and its dry matter content.

In a particularly advantageous manner, the said composition has a pH of between about 7 and 9, the measurement of the pH being carried out after adjusting the dry matter content of the said composition to a value of 40%, this being by any dilution or concentration means available to persons skilled in the art.

The Applicant Company in fact considers as novel compositions as envisaged here, in particular isosorbide compositions having simultaneously such a stability of at least two months and such a pH, measured as described above, in the abovementioned ranges.

The novel composition according to the invention may also be characterized in that it contains, in particular, from 0.0001 to 2% of an improving agent as described above, these percentages being expressed by dry weight of improving agent relative to the dry weight of the internal dehydration product of a hydrogenated sugar, for example isosorbide, predominantly present in the composition.

According to a first variant, the said composition contains from 0.001 to 2%, preferably from 0.002 to 1.5% and still more preferably from 0.003 to 1.5% of an improving agent, it being possible for the latter in particular to consist of $NaBH_4$ or of an antioxidant.

In the case of the use of an improving agent consisting of a boron-containing compound such as $NaBH_4$ containing about 28.6% boron, the said composition can therefore contain from about 0.00029 to 0.572% of boron. These percentages of boron will be higher and up to about 1% if a compound such as $LiBH_4$, which is more rich in boron (about 49.7%), is used in place of $NaBH_4$.

If account is taken of other elements such as nitrogen, sodium, potassium, phosphorus or sulphur, which may be contained to a greater or lesser degree in the improving agents used according to the invention, their presence in the resulting composition can also be highly variable but in any case will be generally at most equal to about 1% as well.

This will be necessarily the case when, according to a second variant, the composition according to the invention will contain even lower levels, i.e. from 0.0001 to 0.5%, preferably from 0.0003 to 0.3%, and in particular from 0.0003 to 0.1%, of an improving agent, it being possible for the latter in particular to consist of a reducing agent (including $NaBH_4$) or of an anti-acid agent (including an alkaline agent).

The Applicant Company in fact considers as novel compositions as envisaged here, in particular isosorbide compositions which contain from 0.0001 to 1% of an element chosen from the group comprising boron, sodium, potassium, phosphorus, sulphur or nitrogen, these percentages being expressed by dry weight/dry weight in the same manner as that described above for the improving agents as such.

These compositions, in particular of isosorbide, may in particular contain from 0.0001 to 0.01% of one of the abovementioned elements.

Such compositions may in particular be used for the preparation of polymeric or nonpolymeric, biodegradable or non-biodegradable products or mixtures intended for the chemical, pharmaceutical, cosmetic or food industries.

The present invention will be described in even greater detail with the aid of the following examples which are not at all limiting.

EXAMPLE 1

1 kg of a sorbitol solution containing 70% DM, marketed by the applicant under the name "NEOSORB® 70/02" and 7 g of concentrated sulphuric acid are introduced into a jacketed stirred reactor. The mixture obtained is heated under vacuum (pressure of about 100 mbar) for 5 hours so as to remove the water contained in the initial reaction medium and that obtained from the sorbitol dehydration reaction.

The crude reaction product is then cooled to around 100° C. and then neutralized with 11.4 g of a 50% sodium hydroxide solution. The isosorbide composition thus neutralized is then distilled under vacuum (pressure of less than 50 mbar).

The slightly coloured (light yellow colour) crude isosorbide distillate is then dissolved in distilled water so as to obtain a solution containing 40% DM.

This solution is then percolated on a "CECA DC 50" granular activated charcoal column at a rate of 0.5 BV/h (Bed Volume/hour). The decolorized isosorbide composition thus obtained is then passed, at a rate of 2 BV/h, successively over a column of "PUROLITE C 150 S" strong cationic resin and then a column of "AMBERLITE IRA 910" strong anionic resin.

The isosorbide solution is then directly concentrated under vacuum. The molten mass obtained crystallizes on cooling in the form of a "massed product" consisting of large crystals which are then ground in order to obtain a white powder having a moisture content of 0.3%.

Its respective contents of formic acid and monoanhydrohexoses are less than 0.0005% (5 ppm), each expressed by dry weight relative to the dry weight of the said composition.

20 g of this massed product of isosorbide are directly introduced into a glass container having a capacity of 50 ml which, after having been hermetically closed, is placed in an oven maintained at 40° C.

After 1 month of storage under these conditions, the isosorbide composition has a formic acid content of 1000 ppm and a content of monoanhydrohexoses of about 7000 ppm.

The "massed product" of isosorbide thus tested cannot therefore be considered as being stable, for the purposes of the present invention.

EXAMPLE 2

In this example, in accordance with the invention, there is recovered a fraction of the isosorbide solution directly derived, after distillation, from the treatment consisting of passing over activated charcoal and then resins as described in EXAMPLE 1, a solution whose dry matter content and isosorbide purity were measured.

As soon as it is recovered, there is introduced into the said fraction a quantity of $NaBH_4$ corresponding to 0.005% (50 ppm) by weight of the weight of isosorbide contained in the said fraction (dry weight/dry weight) and then the concentration step is directly carried out, this being under the same conditions as those described in EXAMPLE 1.

The massed product obtained directly after cooling has characteristics of purity (about 99.1%) and of content of formic acid and of monoanhydrohexoses which are logically of the same order as those of the massed product obtained during EXAMPLE 1.

However, after 1 month of storage under the same conditions as those described in EXAMPLE 1, the isosorbide composition thus adjuvanted with NaBH4 after distillation still has respective contents of formic acid and monoanhydrohexoses of less than 5 ppm.

This composition can therefore be considered as being stable for the purposes of the present invention.

Additional measurements have in fact shown that, after more than 6 months of storage under the same conditions, this same composition still had a formic acid content of less than 5 ppm and a content of monoanhydrohexoses significantly less than 50 ppm. Accordingly, this composition has a stability of at least six months for the purposes of the invention.

EXAMPLE 3

In this example, not in accordance with the invention, there is recovered a fraction of the crude reaction product directly derived from the neutralization step as described in EXAMPLE 1, a neutralized crude reaction product whose dry matter content and isosorbide purity were measured.

As soon as it is recovered, there is introduced into the said fraction a quantity of $NaBH_4$ corresponding to 0.02% (200 ppm) of the isosorbide contained in the said fraction (dry weight/dry weight) and then the steps of distillation under vacuum, of purification on activated charcoal and then resins, of concentration and of cooling as described in EXAMPLE 1 are directly carried out.

The massed product obtained directly after cooling has characteristics of purity and of content of formic acid and of monoanhydrohexoses which are of the same order as those of the massed product obtained during EXAMPLE 2.

However, after 1 month of storage under the same conditions as those described in EXAMPLE 1, the isosorbide composition thus obtained has a formic acid content of 1200 ppm and a content of monoanhydrohexoses content of about 5000 ppm.

This example shows that the use of a product such as $NaBH_4$ before the actual distillation step does not make it possible, in the end, to confer on the resulting isosorbide composition a stability character for the purposes of the present invention.

EXAMPLE 4

In this example, not in accordance with the invention, a massed product is obtained under the same conditions as those of EXAMPLE 1 except that all the steps subsequent to step b) of purification are carried out in an inert atmosphere, under nitrogen.

The massed product has characteristics of formic acid and monoanhydrohexose purity and content which are of the same order as those of the massed product obtained in EXAMPLE 1.

However, after 1 month of storage under the same conditions as those of EXAMPLE 1, the isosorbide composition thus obtained has a formic acid content of 700 ppm and a content of monoanhydrohexoses of about 6000 ppm.

This example shows that the sole use of nitrogen gas, even after the distillation step, does not make it possible, in the end, to confer on the resulting isosorbide composition a stability character for the purposes of the present invention.

EXAMPLE 5

In this example, in accordance with the invention, the procedure is carried out as described in EXAMPLE 2, except that:
1) after its passage over activated charcoal and then resins, the distillate is treated with 5% (dry weight/dry weight) of powdered activated charcoal "NORIT SX +" at 20° C. for 1 hour, and
2) 50 ppm of respectively $NaBH_4$, morpholine, BHT or vitamin C are directly introduced into the distillate thus treated, before concentration.

Each of the four massed products obtained directly after the concentration and cooling steps was stored under the same conditions as those described in EXAMPLE 1.

After 1 or 2 months of storage at 40° C., none of these four products saw its formic acid content reach the value of 5 ppm or its content of monoanhydrohexoses reach the value of 50 ppm.

Remarkably, tests carried out for 6 months and more under the same conditions on the massed products derived from the distillates treated with $NaBH_4$ or morpholine moreover showed that this stability could be maintained at least for this duration.

Isosorbide compositions are thus available which have a stability of at least two months, in particular of at least six months.

EXAMPLE 6

A decolorized and purified isosorbide solution is prepared as described in EXAMPLE 1.

This solution is, after passing over a strong cationic resin and then a strong anionic resin, directly concentrated under vacuum, to a dry matter content of about 85%.

The pH of this isosorbide composition, measured after adjusting its dry matter content to a value of 40% by dilution in distilled water, is of the order of 5.0.

It was then observed, during a storage test performed as described above at 40° C., that such a composition could not be considered as being stable for the purposes of the present invention.

Isosorbide compositions in accordance with the invention are prepared by introducing, into an isosorbide solution which has been decolorized, purified and concentrated to 85% as described above and immediately after the concentration step, small quantities of improving agent consisting respectively of:
- 0.0002% (2 ppm) of $NaBH_4$, or
- 0.0010% (10 ppm) of $NaBH_4$, or
- 0.0005% (5 ppm) of NaOH, or
- 0.0012% (12 ppm) of $NaBO_2$, or
- 0.0015% (15 ppm) of $Na_2HPO_4$.

The pH of the compositions thus obtained varies from about 6.6 to 8.6.

The Applicant Company then observed, during storage tests performed at 40° C. as described above, that all these compositions could not only be considered as being stable for the purposes of the present invention, but further that this stability was of at least two months.

It has already been verified in some of the said compositions that this stability was of at least three months, or even six months or one year.

Accordingly, it is observed that the use of very small quantities of improving agents, i.e. at most equal to 0.1% (dry weight/dry weight), in particular between 0.0001% (1 ppm) and 0.01% (100 ppm) and including of less than 0.005% (50 ppm), made it possible to have a simple and inexpensive means of stabilizing compositions of the type in question, this means being moreover generally capable of satisfying the technical and/or regulatory constraints to which the said compositions may be subjected.

Without wishing to be bound by any theory, the Applicant Company considers that the effect caused by such a use on the pH of the said compositions may, directly or indirectly, play, at least partially, a rôle in the increase in the stability of the said compositions, in any case in their specific stability at ambient or moderate temperature (40° C.).

The invention claimed is:

1. A method for improving stability of a composition of internal dehydration product of a hydrogenated sugar, comprising:
   a) a step of distilling a medium containing the said internal dehydration product in order to obtain a distillate enriched in this product,
   b) optionally, at least one subsequent step of purifying the distillate thus obtained,
   c) a subsequent step of bringing the distillate obtained during step a), which has been optionally subjected to step b), into contact with an agent capable of improving the stability of the internal dehydration product predominantly contained in the distillate, the said agent not being in gaseous form,
   d) optionally, a subsequent step of shaping the resulting composition of internal dehydration product of a hydrogenated sugar,
   wherein the agent is used in step (c) in an amount of 0.0001 to 0.1% these percentages being expressed by dry weight of the said agent relative to the dry weight of the internal dehydration product of a hydrogenated sugar predominantly present in the distillate, and
   wherein the agent used in step c) is selected from the group consisting of reducing agents, antioxidants, oxygen scavengers, anti-acid agents, and mixtures thereof.

2. The method according to claim 1, wherein the agent used in step c) is selected from the group consisting of compounds based on boron, compounds based on sodium, compounds based on potassium, compounds based on phosphorus, compounds based on nitrogen, compounds based on sulphur, aromatic compounds, compounds containing at least one alcohol functional group and any mixtures of at least any two of these products.

3. The method according to claim 1, wherein the agent consists of sodium borohydride ($NaBH_4$) or an antioxidant.

4. The method according to claim 1, wherein the agent is used in an amount of 0.0003 to 0.1%.

5. The method according to claim 4, wherein the agent is used in an amount of 0.0003 to 0.01%.

6. The method according to claim 4, wherein the agent consists of a reducing agent or of an anti-acid agent, the anti-acid agent being selected from alkaline agents.

7. The method according to claim 6, wherein the agent is a sodium salt.

8. The method according to claim 1, wherein the agent used in step c) has solubility in water at 20° C. at least equal to 0.01%.

9. The method according to claim 1, wherein step a) of distillation is followed by a step b) of purification, during which the distillate is treated, in any order, with at least one activated charcoal and with at least one ionic or nonionic resin.

10. The method according to claim 1, comprising at least one concentration step carried out, completely or partly, prior to or simultaneously with step c).

11. The method according to claim 1, wherein the agent used in step c) has solubility in water at 20° C. at least equal to 0.1%.

12. The method according to claim 1, wherein step a) of distillation is followed by a step b) of purification during which the distillate is treated, in any order, with at least one activated charcoal and with at least one ionic or nonionic resin.

* * * * *